United States Patent
Alther

(10) Patent No.: US 6,534,296 B1
(45) Date of Patent: Mar. 18, 2003

(54) PREPARING ORGANOCLAY-ENZYME COMPLEXES USING A QUATERNARY IONIC COMPOUND AND MINERAL

(75) Inventor: George Alther, Fernadale, MI (US)

(73) Assignee: Biomin, Inc., Ferndale, MI (US)

( * ) Notice: Subject to any disclaimer, the term of this patent is extended or adjusted under 35 U.S.C. 154(b) by 0 days.

(21) Appl. No.: 09/261,373

(22) Filed: Mar. 3, 1999

(51) Int. Cl.⁷ .......................... C12N 11/14; C12N 11/02
(52) U.S. Cl. ...................................... 435/176; 435/177
(58) Field of Search ............................... 435/176, 177, 435/180, 174

(56) References Cited

U.S. PATENT DOCUMENTS

| | | | |
|---|---|---|---|
| 3,066,026 A | 11/1962 | Shaler | 426/13 |
| 3,650,967 A * | 3/1972 | Johnson | 252/135 |
| 3,669,841 A | 6/1972 | Miller | 435/176 |
| 3,953,292 A | 4/1976 | Burns | 435/176 |
| 4,004,979 A * | 1/1977 | Avrameas et al. | 435/176 |
| 4,169,014 A * | 9/1979 | Goldberg | 435/182 |
| 4,605,621 A * | 8/1986 | Pinnavaia et al. | 435/177 |
| 4,818,695 A | 4/1989 | Eigtved | 435/134 |
| 5,773,266 A * | 6/1998 | Bosley et al. | 435/136 |

* cited by examiner

Primary Examiner—David M. Naff
(74) Attorney, Agent, or Firm—Dierker & Glassmeyer, P.C.

(57) ABSTRACT

Immobilized enzymes are prepared in a one-step operation by simultaneously adding an aqueous enzyme (for example urease) to a quaternary ionic compound and a mineral (for example bentonite and a quaternary amine) while in a mixer. This one step operation results in an enzyme clad organoclay. A paste may be formed in the mixer which can be extruded to form noodles that are air dried. Immobilized enzymes may alternately be prepared by adding aqueous enzyme to an already formed organoclay.

9 Claims, No Drawings

PREPARING ORGANOCLAY-ENZYME COMPLEXES USING A QUATERNARY IONIC COMPOUND AND MINERAL

FIELD OF THE INVENTION

The present invention relates to specific novel organoclay-enzyme compositions, wherein the enzymes are immobilized without inhibiting their activity. The invention relates to an economic method of preparation of enzyme clad organoclay.

BACKGROUND OF THE INVENTION

Enzymes are known to be active and highly selective catalysts for many applications involving aqueous solutions of substrate compounds. An enzyme composite is rendered insoluble, thus amenable for reuse, when fixed upon a water-insoluble support U.S. Pat. No. 3,953,292 describes how to directly attach enzymes by covalently bonding them to an organic polymeric matrix or to a porous inorganic solid. Particulate insoluble enzymatically active enzymes were produced with a solid siliceous support material including glass. The siliceous support is reacted with certain organosilanes, attaching the enzymes to the reacted organosilanes with a crosslinking agent such as a dialdehyde like glutacaldehyde. In this patent heat activated attapulgite was used as a support. The enzyme was coupled to the attapulgite aggregates by an intermediate silane coupling agent. U.S. Pat. No. 3,669,841 describes a similar method. Clay-enzyme reactions were patented as far back as 1962. U.S. Pat. No. 3,066,026 describes enzyme clad clays used in the brewing of beer.

U.S. Pat. No. 3,650,967 describes dry mixing an enzyme such as protease with a salt such as sodium tripolyphosphate, an organic polymer such as carboxymethyl cellulose, and a clay mineral in a rotating drum. This results in granules which are incorporated into dry laundry detergents. It is not reported whether the enzyme attached to the clay during processing.

U.S. Pat. No. 4,605,621 describes a method of immobilizing enzymes on organoclays to confer stability. In this manner the enzyme is available for the projected use, without its catalytic ability being limited by the immobilization mechanism. This patent reports that the enzymes are bound to the organoclay by some sort of hydrophobic bonding. This method is pH independent. The patent teaches how to prepare an organoclay by mixing a quaternary amine such as hexadecyl trimethyl ammonium bromide with bentonite in a glass jar, including washing of the clay, several hours of equilibration, filtering and washing again with distilled water, followed by freezing and freeze drying. Once the organoclay is dry, the organoclay powder is introduced into a glass jar, where the enzyme powder, urease in this case, was previously dissolved in water at a 1% (w/w) addition level. The authors found that they could add urease at a level as high as 40% by weight of the organoclay, with resulting immobilization. Needless to say, this process is far too complicated and expensive to be put into practice in industry.

U.S. Pat. No. 4,818,695 teaches how microbial lipase derived from the thermophilic mucor species used for the esterification of fats is immobilized on an ion exchange resin. The enzyme powder is dissolved in water, and the resulting slurry is mixed with a particulate macroporous weak anion exchange resin. The resin is then filtered out of the slurry and dried. By providing a specified proportion of water content in the final immobilized preparation, continuous esterification of fats without a solvent is possible. This process results in a strong bond between the lipase and ion exchange resin. However, it takes 5–8 hours of contact time between the resin and the lipase to remove 75% of the enzyme from water and immobilize it on the resin, which is not economical in practice. The resin must then be rigorously washed with water to improve the performance of the final product. Drying of the resin, which must be done down to a moisture content of 20%, is done in a vacuum drying oven, fluid bed or some other drying method. Once the enzyme clad resin is introduced in the esterification process, a continuous, low cost method is at work. However, the preparation of the resin is economically unattractive.

SUMMARY OF THE INVENTION

The present invention solves t he problems enumerated above by providing a method for immobilizing enzymes, comprising the step of simultaneously mixing an aqueous enzyme to be immobilized with a quaternary ionic compound and a mineral; wherein the mineral and the quaternary ionic compound react simultaneously with the aqueous enzyme to form an organoclay material having the enzyme immobilized thereon.

DETAILED DESCRIPTION OF THE PREFERRED EMBODIMENTS

Soil eco-enzymes such as urease are immobilized on the organic matter portion of organic mineral complexes in soil. Such complexation confers stability to the urease. When glucose oxidase is immobilized on an organoclay, hydrophobic bonding occurs. The enzyme is strongly bound to the protruding end of the quaternary amine regardless of the pH. The final product exhibits a pH profile similar to the free enzyme (enzyme not immobilized).

Organoclay clad enzymes were prerpared in the following manner: Bentonite was mixed with quaternary amine of the di-methyl dihydrogenated tallow ammonium chloride type surfactant, in a bowl. A small amount of water was also added, and the paste was passed through a laboratory meatgrinder several times to assure thorough mixing. The resulting noodles are then air dried and ground into granules or milled into a free flowing powder.

To further illustrate the present invention, the following examples are given. It is to be understood that these examples are provided for illustrative purposes and are not to be construed as limiting the scope of the present invention.

EXAMPLE 1

Urease Type IV, derived from Jack Beans and purchased from Sigma Chemical Co. was used in this experiment. This enzyme had an activity of 50,000 micro M units gram-1. The enzymatic reactions were carried out in a buffer solution containing 0.1 M $NaH_2PO_4$ and $1\times10^{-3}$ M ethylene diamine tetraacetic acid (EDTA). The buffer solution was adjusted to pH 6.9 with NaOH. Urease is an enzyme that converts to urea, ammonia and carbon dioxide. Therefore the amount of ammonia produced is a direct measure of the enzyme activity.

The urease was added to 3 organoclays with varying levels of quaternary amines, at a 1% (w/w) level. A solution containing 1 mg urease mL-1 buffer was prepared fresh before each experiment. The organoclay/enzyme complex was prepared in the following manner: 1 ml of enzyme solution was added to organoclay in 4 ml buffer.

The enzyme/organoclay mixture was then shaken gently for 18–20 hours at 20 degree C. For comparison, 1 ml of enzyme solution was added to 4 ml of buffer without the organoclay (referred to as "free enzyme") and treated in the same fashion. Ammonia produced from 1 mmole of substrate after 24 hours was analyzed for free and immobilized urease.

Table 1 below shows that urease activity was high on all 3 clays. Clay 1, 45% quaternary amine, was equal to the free enzyme. Clay 2 was 75% active. Clay 3 was 90% active. With this clay a different bentonite and 30% quaternary amine were used.

TABLE 1

Activity of urease either free in solution or mixed with organo-clays.[a]

| Sample | $NH_3$ produced[b] (mmoles) |
|---|---|
| Free enzyme | 2.0 |
| PC - 1 | 2.1 |
| PTI - Sy | 1.8 |
| PT - IE | 1.5 |

[a]Urease was added to clays at a 1% (w/w) level.
[b]Maximum theoretical yield is 2.0 mmoles; assay time was 3.5 hours; assay volume was 40 ml of 25 molar urea.

EXAMPLE 2

The same method was used to prepare the organoclay as in Table 1, but this time the aqueous sample with the enzyme was added at a 1% loading level to the clay during processing, i.e. when the amine and water where mixed with the bentonite. This is a one step process. The enzyme clad organoclay is then passed through a meat grinder, allowed to dry, and milled or granulated. The percent immobilization was estimated by measuring urease activity in the supernatant of the organoclay/enzyme mixtures. If all the enzyme was immobilized, the enzyme activity in the supernatant would be zero. Table 2 shows the results.

TABLE 2

Estimated degree of urease immobilization in organo-clays.[a]

| Sample | $NH_3$ produced[b] (mmoles) | Percent Immobilization |
|---|---|---|
| Free | 0.4 | 0 |
| PTI - SY | 0.125 | 69 |
| PT - IE | 0.0375 | 91 |

[a]Estimated from urease activity in supernatant of clay-enzyme mixtures.
[b]Maximum theoretical yield is 1.25 mmoles; assay time was 2 hours; assay volume was 25 ml of 25 mmolar urea.

These results using this method are not quite as good as the ones from Table 1, but a high degree of immobilization is still apparent. Clay 2 is clad with 36% amine, while Clay 1 was treated with 30% quaternary amine. Clay 2 showed more activity than Clay 1, suggesting that increased amine content, up to a certain level, results in increased enzyme immobilization.

Comparing Table 1 results with Table 2 results also shows that different bentonites result in different enzyme immobilization activity. The same observation holds for the use of different quaternary amines.

The one step method used in Table 2 is economically feasible, since this method of manufacturing organoclay has been in use since 1967, but was never used to immobilize enzymes. Potential use can be the conversion of or the metabolic pathway from ethanol, which is used in antifreeze, to acetaldehyde to acetate to carbon dioxide. This process would include in the first step alcohol dehydrogenase, and in the second step aldehyde dehydrogenase. The acetate can then be oxidized to carbon dioxide using acetyl -Co A synthebase.

What is claimed is:

1. A method for immobilizing enzymes, comprising the steps of:

simultaneously mixing an aqueous enzyme to be immobilized with a quaternary ionic compound and a mineral to form a paste;

passing the paste through a grinder that extrudes the paste to form noodles; and air drying the noodles;

wherein the mineral and the quaternary ionic compound react simultaneously with the aqueous enzyme to form an organoclay material having the enzyme material thereon.

2. A method according to claim 1, wherein the mineral is selected from the group consisting of bentonite, montmorillonite, saponite, sepiolite, attapulgite, vermiculite, kaolinite, illite, clinoptilolite, mordenite, ettringite, chabazite and combinations thereof.

3. A method as in claim 1, wherein the quaternary ionic compound comprises a quaternary amine.

4. A method as in claim 1, wherein the quaternary ionic compound comprises a pyridinium compound.

5. A method as in claim 1, wherein the enzyme is urease.

6. The method as defined in claim 1, further comprising the step of processing the dried noodles by at least one of: grinding into granules; and milling into a free flowing powder.

7. A method for immobilizing enzymes, comprising the steps of:

simultaneously mixing an aqueous enzyme to be immobilized with a quaternary ionic compound and a mineral material to form a paste, passing the paste through a grinder that extrudes the paste to form noodles; and air drying the noodles;

wherein the mineral material and the quaternary ionic compound react simultaneously with the aqueous enzyme to form an organoclay material having the enzyme immobilized thereon, wherein the mineral is selected from the group consisting of bentonite, mortmorillonite, saponite, sepiolite, attapulgite, vermiculite, kaolinite, illite, clinoptilolite, mordenite, ettringite, chabazite and combinations thereof;

and wherein the quaternary ionic compound comprises a quaternary amine.

8. A method as in claim 7, wherein the enzyme is urease.

9. The method as defined in claim 7, further comprising the step of processing the dried noodles by at least one of: grinding into granules; and milling into a free flowing powder.

* * * * *